United States Patent [19]
Morrissey

[11] Patent Number: 5,741,658
[45] Date of Patent: Apr. 21, 1998

[54] QUANTITATIVE CLOTTING ASSAY FOR ACTIVATED FACTOR VII

[75] Inventor: James H. Morrissey, Oklahoma City, Okla.

[73] Assignee: Oklahoma Medical Research Foundation, Oklahoma City, Okla.

[21] Appl. No.: 463,931

[22] Filed: Jun. 5, 1995

Related U.S. Application Data

[63] Continuation-in-part of Ser. No. 683,682, Apr. 10, 1991, Pat. No. 5,472,850.

[51] Int. Cl.$^6$ .................................................. C12Q 1/37
[52] U.S. Cl. .................... 435/23; 435/212; 435/226; 435/13; 436/16; 436/69; 530/380; 530/384
[58] Field of Search ........................ 435/13, 23, 212, 435/226; 436/16, 69; 530/380, 384

[56] References Cited

U.S. PATENT DOCUMENTS

| | | | |
|---|---|---|---|
| 4,479,938 | 10/1984 | Thomas | 514/8 |
| 5,180,583 | 1/1993 | Hedner | 514/2 |
| 5,298,599 | 3/1994 | Rezaie et al. | 530/350 |
| 5,346,991 | 9/1994 | Roy et al. | 530/350 |

FOREIGN PATENT DOCUMENTS

| | | |
|---|---|---|
| 0225160 | 6/1987 | European Pat. Off. . |
| 0278776 | 3/1988 | European Pat. Off. . |
| 8807543 | 10/1988 | WIPO . |
| 8809817 | 12/1988 | WIPO . |
| WO93/23074 | 11/1993 | WIPO . |

OTHER PUBLICATIONS

Bach, et al., "Factor VII binding to tissue factor in reconstituted phospholipid vesicles: induction of cooperativity by phosphatidylserine," *Biochemistry*, 25:4007–4020 (1986).

De Sousa, et al., "Factor VII hyperactivity in acute myocardial thrombosis. a relation to the coagulation activation," *Thrombosis Research*, 51:165–173 (1988).

Fair, Daryl S., "Quantitation of Factor VII in the plasma of normal and Warfarin-treated individuals by radioimmunoassay," *Blood* 62:784–791 (1983).

Fiore, et al., "An unusual antibody that blocks tissue factor/Factor VIIa function by inhibiting cleavage only of macromolecular substrates," *Blood* 80:3127–3134 (1992).

Fisher, et al., "Cloning and expression of human tissue factor cDNA," *Thrombosis Research*, 48:89–99 (1987).

Gordon, et al., "Augmented Hageman factor and prolactin titers, enhanced cold activation of factor VII, and spontaneous shortening of prothrombin time in survivors of myocardial infarction," *J. Lab. Clin. Med.*, 109:409–413 (1987).

Hagen, et al., "Characterization of a cDNA coding for human factor VII," *Proc Natl Acad Sci USA* 83:2412–2416 (1986).

Hapak, et al., "The location of the active site of Factor VIIa above the membrane surface is altered by either full–length or truncated tissue factor," *FASEB Journal* 6:A330, Abstract No. 1900 (1992).

Hedner, et al., "Use of human factor VIIa in the treatment of two hemophilia A patients with high–titer inhibitors," *J Clin Invest* 71:1836–1841 (1983).

Hedner, Ulla, "Experiences with recombinant Factor VIIa in haemophiliacs," *Biotechnology of Plasma Proteins Curr Stud Hematol Blood Transf* 58:63–68 (1991), Switzerland.

Hoffman, et al., "Factor VII activity state in coronary artery disease," *J. Lab. Clin. Med.*, 111:475–481 (1988).

Kisiel, et al., "Activation of bovine Factor VII (Proconvertin) by Factor XII$_a$ (activated Hageman factor)," *Biochemistry* 16:4189–4194 (1977).

Lawson, et al., "The evaluation of complex–dependent alterations in human Factor VIIa," *J. Biol. Chem.*, 267:4834–4843 (1992).

Mackman, et al., "Complete sequence of the human tissue factor gene, a highly regulated cellular receptor that initiaties the coagulation protease cascade," *Biochemistry*, 28:1755–1762 (1989).

Masys, et al., "Activation of human Factor VII by activated Factors IX and X," *Blood* 60:1143–1150 (1982).

Mitropoulos, "Hypercoagulability and Factor VII in hypertriglyceridemia," *Seminars in Thrombosis and Hemostasis*, 14:246–251 (1988).

Morrissey, et al., "Molecular cloning of the cDNA for tissue factor, the cellular receptor for the initiation of the coagultion protease cascade," *Cell* 50:129–135 (1987).

Morrissey, et al., "Monoclonal antibody analysis of purified and cell–associated tissue factor," *Thrombosis Research* 52:247–261 (1988).

Morrissey, et al., "Quantitation of activated Factor VII levels in plasma using a tissue factor mutant selectively deficient in promoting Factor VII activation," *Blood* 81:734–744 (1993).

Nakagaki, et al., "Activation of human Factor VII by the prothrombin activator from the venom of *Oxyuranus scutellatus* (Taipan Snake)," *Thrombosis Research* 65:105–116 (1992).

Nemerson, "Tissue factor and hemostasis," *Blood,* 71:1–8 (1988).

Neuenschwander, P.F. and Morrissey, J.H., "Deletion of the membrane anchoring region of tissue factor abolishes autoactivation of Factor VII but not cofactor function," *J Biol Chem* 267:14477–14482 (1992).

Paborsky, et al., "Purification of recombinant human tisue factor," *Biochemistry,* 28:8072–8077 (1989).

Paborsky and Harris, "Post–translational modifications of recombinant human tissue factor," *Thrombosis Research,* 60:367–376 (1990).

Paborsky, et al., "Lipid association, but not the transmembrane domain, is required for tissue factor activity," *J Biol Chem* 266:21911–21916 (1991).

Poggio, et al., "Factor VII clotting assay: influence of different thromboplastins and Factor VII–deficient plasmas," *Thrombosis Haemostasis,* 65:160–164 (1991).

Radcliffe, et al., "Activation and control of Factor VII by activated Factor X and thrombin," *J Biol Chem* 250:388–395 (1975).

Rezaie, et al., "Expression and purification of a soluble tissue factor fusion protein with an epitope for an unusual calcium–dependent antibody," *Protein Expression and Purification* 3:453–460 (1992).

Ruf, et al., "The isolated extracellular domain of tissue factor is functional on phopholipid surfaces," *Thrombosis & Haemostasis* 62:347 (1989).

Ruf, et al., "Characterization of Factor VII association with tissue factor in solution," *J Biol Chem* 266:15719–15725 (1991).

Ruf, et al., "Phospholipid–independent and –dependent interactions required for tissue factor receptor and cofactor function," *J Biol Chem* 266:2158–2166 (1991).

Sakai, et al., "Formation of tissue factor activity following incubation of recombinant human tissue factor apoprotein with plasma lipoproteins," *Thrombosis Research* 60:213–222 (1990).

Scarabin, et al., "Is Factor VII activation in pregnant women relevant to fetal growth retardation?," *Thrombosis Research,* 45:845–850 (1987).

Scarpati, et al., "Human tissue factor: cDNA sequence and chromosome localization of the gene," *Biochemistry,* 26:5234–5238 (1987).

Seligsohn, et al., "Coupled amidolytic assay for Factor VII: its use with a clotting assay to determine the activity state of Factor VII," *Blood* 52:978–988 (1978).

Shigematsu, et al., "Expression of human soluble tissue factor in yeast and enzymatic properties of its complex with Factor VIIa," *J Biol Chem* 267:21329–21337 (1992).

Spicer, et al., "Isolation of cDNA clones coding for human tissue factor: primary structure of the protein and cDNA," *Proc. Natl. Acad. Sci. USA,* 84:5148–5152 (1987).

Teitel, Jerome M., "The Factor VIII bypassing activity of prothrombin complex concentrates: the roles of VIIa and of endothelial cell tissue factor," *Thrombosis Haemostasis* 66:559–564 (1991).

Telgt, et al., "Mechanism by which recombinant Factor VIIa shortens the aPTT: activation of Factor X in the absence of tissue factor," *Thrombosis Research* 56:603–609 (1989).

Waxman, et al., "Tissue factor and its extracellular soluble domain: the relationship between intermolecular association with Factor VIIa and enzymatic activity of the complex," *Biochem* 31:3998–4003 (1992).

Zur, et al., "The dual role of Factor VII in blood coagulation," *J. Biol. Chem.,* 257:5623–5631 (1982).

*Primary Examiner*—Robert A. Wax
*Assistant Examiner*—Enrique D. Longton
*Attorney, Agent, or Firm*—Sidley & Austin

[57]     ABSTRACT

An kit for an assay for measuring activated factor VII (factor VIIa) is disclosed which employs a reagent comprising truncated tissue factor (tTF), a soluble mutant form of tissue factor (TF) that retains the cofactor function of TF toward factor VIIa, but does not support the conversion of factor VII to VIIa. As a result, the tTF assay for factor VIIa is free from interference from factor VII in the plasma and is therefore specific for factor VIIa. The assay is much simpler than existing assays, because it is a single-stage clotting assay performed almost identically to a prothrombin time (PT) assay. It is also considerably more sensitive than current assays for factor VIIa in plasma. Since the tTF assay is calibrated against a factor VIIa standard, it yields an absolute concentration of factor VIIa in ng/ml.

28 Claims, 5 Drawing Sheets

```
                                                   M  E  T  P  A  W
  1 CGTTCCGCTC GATCTCGCCG CCAACTGGTA GACATGGAGA CCCCTGCCTG

P  R  V    P  R  P    E  T  A  V    A  R  T    L  L  L
 51 GCCCCGGGTC CGCGCCCCG AGACCGCCGT CGCTCGGACG CTCCTGCTCG

G  W  V  F    A  Q  V    A  G  A    S  G  T  T    N  T  V
101 GCTGGGTCTT CGCCCAGGTG GCCGGCGCTT CAGGCACTAC AAATACTGTG

A  A  Y    N  L  T  W    K  S  T    N  F  K    T  I  L  E
151 GCAGCATATA ATTTAACTTG GAAATCAACT AATTTCAAGA CAATTTTGGA

W  E  P    K  P  V    N  Q  V  Y    T  V  Q    I  S  T
201 GTGGGAACCC AAACCCGTCA ATCAAGTCTA CACTGTTCAA ATAAGCACTA

K  S  G  D    W  K  S    K  C  F    Y  T  T  D    T  E  C
251 AGTCAGGAGA TTGGAAAAGC AAATGCTTTT ACACAACAGA CACAGAGTGT

D  L  T    D  E  I  V    K  D  V    K  Q  T    Y  L  A  R
301 GACCTCACCG ACGAGATTGT GAAGGATGTG AAGCAGACGT ACTTGGCACG

V  F  S    Y  P  A    G  N  V  E    S  T  G    S  A  G
351 GGTCTTCTCC TACCCGGCAG GGAATGTGGA GAGCACCGGT TCTGCTGGGG

E  P  L  Y    E  N  S    P  E  F    T  P  Y  L    E  T  N
401 AGCCTCTGTA TGAGAACTCC CCAGAGTTCA CACCTTACCT GGAGACAAAC

L  G  Q    P  T  I  Q    S  F  E    Q  V  G    T  K  V  N
451 CTCGGACAGC CAACAATTCA GAGTTTTGAA CAGGTGGGAA CAAAAGTGAA

V  T  V    E  D  E    R  T  L  V    R  R  N    N  T  F
501 TGTGACCGTA GAAGATGAAC GGACTTTAGT CAGAAGGAAC AACACTTTCC

L  S  L  R    D  V  F    G  K  D    L  I  Y  T    L  Y  Y
551 TAAGCCTCCG GGATGTTTTT GGCAAGGACT TAATTTATAC ACTTTATTAT

W  K  S    S  S  S  G    K  K  T    A  K  T    N  T  N  E
601 TGGAAATCTT CAAGTTCAGG AAAGAAAACA GCCAAAACAA ACACTAATGA

F  L  I    D  V  D    K  G  E  N    Y  C  F    S  V  Q
651 GTTTTTGATT GATGTGGATA AAGGAGAAAA CTACTGTTTC AGTGTTCAAG

A  V  I  P    S  R  T    V  N  R    K  S  T  D    S  P  V
701 CAGTGATTCC CTCCCGAACA GTTAACCGGA AGAGTACAGA CAGCCCGGTA

E  C  M    G  Q  E  K    G  E  F    R  E
751 GAGTGTATGG GCCAGGAGAA AGGGGAATTT AGAGAATAAG AATTC
```

FIG. 1

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 2141 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 112..999

( i x ) FEATURE:
        ( A ) NAME/KEY: mat_peptide
        ( B ) LOCATION: 208..996
        ( D ) OTHER INFORMATION: /note= "tissue factor version 1"

( i x ) FEATURE:
        ( A ) NAME/KEY: mat_peptide
        ( B ) LOCATION: 214..996
        ( D ) OTHER INFORMATION: /note= "tissue factor version 2"

( x i ) SEQUENCE DESCRIPTION: SEQ ID NO:1:

```
CGGGCGAACC  CCCTCGCACT  CCCTCTGGCC  GGCCCAGGGC  GCCTTCAGCC  CAACCTCCCC            60

AGCCCCACGG  GCGCCACGGA  ACCCGCTCGA  TCTCGCCGCC  AACTGGTAGA C ATG GAG             117
                                                            Met Glu
                                                            -32

ACC CCT GCC TGG CCC CGG GTC CCG CGC CCC GAG ACC GCC GTC GCT CGG                 165
Thr Pro Ala Trp Pro Arg Val Pro Arg Pro Glu Thr Ala Val Ala Arg
-30              -25              -20              -15
```

| | | | | | | | | | | | | | | | | |
|---|---|---|---|---|---|---|---|---|---|---|---|---|---|---|---|---|
| ACG | CTC | CTG | CTC | GGC | TGG | GTC | TTC | GCC | CAG | GTG | GCC | GGC | GCT | TCA | GGC | 213 |
| Thr | Leu | Leu | Leu | Gly -10 | Trp | Val | Phe | Ala | Gln -5 | Val | Ala | Gly | Ala | Ser | Gly 1 | |
| ACT | ACA | AAT | ACT | GTG | GCA | GCA | TAT | AAT | TTA | ACT | TGG | AAA | TCA | ACT | AAT | 261 |
| Thr | Thr | Asn 5 | Thr | Val | Ala | Ala | Tyr | Asn 10 | Leu | Thr | Trp | Lys | Ser 15 | Thr | Asn | |
| TTC | AAG | ACA | ATT | TTG | GAG | TGG | GAA | CCC | AAA | CCC | GTC | AAT | CAA | GTC | TAC | 309 |
| Phe | Lys 20 | Thr | Ile | Leu | Glu | Trp 25 | Glu | Pro | Lys | Pro | Val 30 | Asn | Gln | Val | Tyr | |
| ACT | GTT | CAA | ATA | AGC | ACT | AAG | TCA | GGA | GAT | TGG | AAA | AGC | AAA | TGC | TTT | 357 |
| Thr 35 | Val | Gln | Ile | Ser | Thr 40 | Lys | Ser | Gly | Asp | Trp 45 | Lys | Ser | Lys | Cys | Phe 50 | |
| TAC | ACA | ACA | GAC | ACA | GAG | TGT | GAC | CTC | ACC | GAC | GAG | ATT | GTG | AAG | GAT | 405 |
| Tyr | Thr | Thr | Asp | Thr 55 | Glu | Cys | Asp | Leu | Thr 60 | Asp | Glu | Ile | Val | Lys 65 | Asp | |
| GTG | AAG | CAG | ACG | TAC | TTG | GCA | CGG | GTC | TTC | TCC | TAC | CCG | GCA | GGG | AAT | 453 |
| Val | Lys | Gln | Thr 70 | Tyr | Leu | Ala | Arg | Val 75 | Phe | Ser | Tyr | Pro | Ala 80 | Gly | Asn | |
| GTG | GAG | AGC | ACC | GGT | TCT | GCT | GGG | GAG | CCT | CTG | TAT | GAG | AAC | TCC | CCA | 501 |
| Val | Glu | Ser 85 | Thr | Gly | Ser | Ala | Gly 90 | Glu | Pro | Leu | Tyr | Glu 95 | Asn | Ser | Pro | |
| GAG | TTC | ACA | CCT | TAC | CTG | GAG | ACA | AAC | CTC | GGA | CAG | CCA | ACA | ATT | CAG | 549 |
| Glu | Phe | Thr 100 | Pro | Tyr | Leu | Glu | Thr 105 | Asn | Leu | Gly | Gln | Pro 110 | Thr | Ile | Gln | |
| AGT | TTT | GAA | CAG | GTG | GGA | ACA | AAA | GTG | AAT | GTG | ACC | GTA | GAA | GAT | GAA | 597 |
| Ser 115 | Phe | Glu | Gln | Val | Gly 120 | Thr | Lys | Val | Asn | Val 125 | Thr | Val | Glu | Asp | Glu 130 | |
| CGG | ACT | TTA | GTC | AGA | AGG | AAC | AAC | ACT | TTC | CTA | AGC | CTC | CGG | GAT | GTT | 645 |
| Arg | Thr | Leu | Val | Arg 135 | Arg | Asn | Asn | Thr | Phe 140 | Leu | Ser | Leu | Arg | Asp 145 | Val | |
| TTT | GGC | AAG | GAC | TTA | ATT | TAT | ACA | CTT | TAT | TAT | TGG | AAA | TCT | TCA | AGT | 693 |
| Phe | Gly | Lys | Asp 150 | Leu | Ile | Tyr | Thr | Leu 155 | Tyr | Tyr | Trp | Lys | Ser 160 | Ser | Ser | |
| TCA | GGA | AAG | AAA | ACA | GCC | AAA | ACA | AAC | ACT | AAT | GAG | TTT | TTG | ATT | GAT | 741 |
| Ser | Gly | Lys 165 | Lys | Thr | Ala | Lys | Thr 170 | Asn | Thr | Asn | Glu | Phe 175 | Leu | Ile | Asp | |
| GTG | GAT | AAA | GGA | GAA | AAC | TAC | TGT | TTC | AGT | GTT | CAA | GCA | GTG | ATT | CCC | 789 |
| Val | Asp 180 | Lys | Gly | Glu | Asn | Tyr 185 | Cys | Phe | Ser | Val | Gln 190 | Ala | Val | Ile | Pro | |
| TCC | CGA | ACA | GTT | AAC | CGG | AAG | AGT | ACA | GAC | AGC | CCG | GTA | GAG | TGT | ATG | 837 |
| Ser 195 | Arg | Thr | Val | Asn | Arg 200 | Lys | Ser | Thr | Asp | Ser 205 | Pro | Val | Glu | Cys | Met 210 | |
| GGC | CAG | GAG | AAA | GGG | GAA | TTC | AGA | GAA | ATA | TTC | TAC | ATC | ATT | GGA | GCT | 885 |
| Gly | Gln | Glu | Lys | Gly 215 | Glu | Phe | Arg | Glu | Ile 220 | Phe | Tyr | Ile | Ile | Gly 225 | Ala | |
| GTG | GTA | TTT | GTG | GTC | ATC | ATC | CTT | GTC | ATC | ATC | CTG | GCT | ATA | TCT | CTA | 933 |
| Val | Val | Phe | Val 230 | Val | Ile | Ile | Leu | Val 235 | Ile | Ile | Leu | Ala | Ile 240 | Ser | Leu | |
| CAC | AAG | TGT | AGA | AAG | GCA | GGA | GTG | GGG | CAG | AGC | TGG | AAG | GAG | AAC | TCC | 981 |
| His | Lys | Cys 245 | Arg | Lys | Ala | Gly | Val 250 | Gly | Gln | Ser | Trp | Lys 255 | Glu | Asn | Ser | |
| CCA | CTG | AAT | GTT | TCA | TAA | AGGAAGCACT | GTTGGAGCTA | CTGCAAATGC | | | | | | | | 1029 |
| Pro | Leu | Asn 260 | Val | Ser | * | | | | | | | | | | | |

```
TATATTGCAC TGTGACCGAG AACTTTTAAG AGGATAGAAT ACATGGAAAC GCAAATGAGT      1089

ATTCGGAGC ATGAAGACCC TGGAGTTCAA AAAACTCTTG ATATGACCTG TTATTACCAT        1149

TAGCATTCTG GTTTTGACAT CAGCATTAGT CACTTTGAAA TGTAACGAAT GGTACTACAA      1209

CCAATTCCAA GTTTTAATTT TTAACACCAT GGCACCTTTT GCACATAACA TGCTTTAGAT      1269
```

```
TATATATTCC  GCACTTAAGG  ATTAACCAGG  TCGTCCAAGC  AAAAACAAAT  GGGAAAATGT   1329

CTTAAAAAAT  CCTGGGTGGA  CTTTTGAAAA  GCTTTTTTTT  TTTTTTTTT   TTGAGACGGA   1389

GTCTTGCTCT  GTTGCCCAGG  CTGGAGTGCA  GTAGCACGAT  CTCGGCTCAC  TTGCACCCTC   1449

CGTCTCTCGG  GTTCAAGCAA  TTGTCTGCCT  CAGCCTCCCG  AGTAGCTGGG  ATTACAGGTG   1509

CGCACTACCA  CGCCAAGCTA  ATTTTTGTAT  TTTTAGTAG   AGATGGGGTT  TCACCATCTT   1569

GGCCAGGCTG  GTCTTGAATT  CCTGACCTCA  GTGATCCACC  CACCTTGGCC  TCCCAAAGAT   1629

GCTAGTATTA  TGGGCGTGAA  CCACCATGCC  CAGCCGAAAA  GCTTTGAGG   GGCTGACTTC   1689

AATCCATGTA  GGAAAGTAAA  ATGGAAGGAA  ATTGGGTGCA  TTTCTAGGAC  TTTTCTAACA   1749

TATGTCTATA  ATATAGTGTT  TAGGTTCTTT  TTTTTTTCAG  GAATACATTT  GGAAATTCAA   1809

AACAATTGGG  CAAACTTTGT  ATTAATGTGT  TAAGTGCAGG  AGACATTGGT  ATTCTGGGCA   1869

GCTTCCTAAT  ATGCTTTACA  ATCTGCACTT  TAACTGACTT  AAGTGGCATT  AAACATTTGA   1929

GAGCTAACTA  TATTTTTATA  AGACTACTAT  ACAAACTACA  GAGTTTATGA  TTTAAGGTAC   1989

TTAAAGCTTC  TATGGTTGAC  ATTGTATATA  TAATTTTTTA  AAAAGGTTTT  TCTATATGGG   2049

GATTTTCTAT  TTATGTAGGT  AATATTGTTC  TATTTGTATA  TATTGAGATA  ATTTATTTAA   2109

TATACTTTAA  ATAAAGGTGA  CTGGGAATTG  TT                                   2141
```

(2) INFORMATION FOR SEQ ID NO:2:

(i) SEQUENCE CHARACTERISTICS:
        (A) LENGTH: 295 amino acids
        (B) TYPE: amino acid
        (D) TOPOLOGY: linear (ii) MOLECULE TYPE: protein (xi) SEQUENCE DESCRIPTION: SEQ ID NO:2:

```
Met  Glu  Thr  Pro  Ala  Trp  Pro  Arg  Val  Pro  Arg  Pro  Glu  Thr  Ala  Val
-32       -30                      -25                 -20

Ala  Arg  Thr  Leu  Leu  Leu  Gly  Trp  Val  Phe  Ala  Gln  Val  Ala  Gly  Ala
     -15                 -10                      -5

Ser  Gly  Thr  Thr  Asn  Thr  Val  Ala  Ala  Tyr  Asn  Leu  Thr  Trp  Lys  Ser
  1             5                      10                      15

Thr  Asn  Phe  Lys  Thr  Ile  Leu  Glu  Trp  Glu  Pro  Lys  Pro  Val  Asn  Gln
            20                      25                      30

Val  Tyr  Thr  Val  Gln  Ile  Ser  Thr  Lys  Ser  Gly  Asp  Trp  Lys  Ser  Lys
            35                      40                      45

Cys  Phe  Tyr  Thr  Thr  Asp  Thr  Glu  Cys  Asp  Leu  Thr  Asp  Glu  Ile  Val
       50                      55                      60

Lys  Asp  Val  Lys  Gln  Thr  Tyr  Leu  Ala  Arg  Val  Phe  Ser  Tyr  Pro  Ala
 65                      70                      75                      80

Gly  Asn  Val  Glu  Ser  Thr  Gly  Ser  Ala  Gly  Glu  Pro  Leu  Tyr  Glu  Asn
                 85                      90                      95

Ser  Pro  Glu  Phe  Thr  Pro  Tyr  Leu  Glu  Thr  Asn  Leu  Gly  Gln  Pro  Thr
                100                     105                     110

Ile  Gln  Ser  Phe  Glu  Gln  Val  Gly  Thr  Lys  Val  Asn  Val  Thr  Val  Glu
            115                     120                     125

Asp  Glu  Arg  Thr  Leu  Val  Arg  Arg  Asn  Asn  Thr  Phe  Leu  Ser  Leu  Arg
        130                     135                     140

Asp  Val  Phe  Gly  Lys  Asp  Leu  Ile  Tyr  Thr  Leu  Tyr  Tyr  Trp  Lys  Ser
145                     150                     155                     160

Ser  Ser  Ser  Gly  Lys  Lys  Thr  Ala  Lys  Thr  Asn  Thr  Asn  Glu  Phe  Leu
```

|  | 165 |  |  |  |  |  | 170 |  |  |  |  | 175 |  |
|---|---|---|---|---|---|---|---|---|---|---|---|---|---|

Ile Asp Val Asp Lys Gly Glu Asn Tyr Cys Phe Ser Val Gln Ala Val
        180                     185                 190

Ile Pro Ser Arg Thr Val Asn Arg Lys Ser Thr Asp Ser Pro Val Glu
        195                 200             205

Cys Met Gly Gln Glu Lys Gly Glu Phe Arg Glu Ile Phe Tyr Ile Ile
    210             215                 220

Gly Ala Val Val Phe Val Val Ile Ile Leu Val Ile Ile Leu Ala Ile
225             230                 235                     240

Ser Leu His Lys Cys Arg Lys Ala Gly Val Gly Gln Ser Trp Lys Glu
            245             250                     255

Asn Ser Pro Leu Asn Val Ser
            260

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..23
        ( D ) OTHER INFORMATION: /note= "synthetic oligonucleotide"

( x i ) SEQUENCE DESCRIPTION: SEQ ID NO:3:

AATTTAGAGA ATAAGAATTC GGG      23

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..19
        ( D ) OTHER INFORMATION: /note= "synthetic oligonucleotide"

( x i ) SEQUENCE DESCRIPTION: SEQ ID NO:4:

CCCGAATTCT TATTCTCTA      19

( 2 ) INFORMATION FOR SEQ ID NO:5:

( i ) SEQUENCE CHARACTERISTICS:
        ( A ) LENGTH: 795 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( v ) FRAGMENT TYPE: N-terminal ( v i ) ORIGINAL SOURCE:
        ( A ) ORGANISM: homo sapiens ( i x ) FEATURE:
        ( A ) NAME/KEY: sig_peptide ( B ) LOCATION: 1..33

( i x ) FEATURE:
    ( A ) NAME/KEY: CDS
    ( B ) LOCATION: 34..786

( i x ) FEATURE:
    ( A ) NAME/KEY: mat_peptide
    ( B ) LOCATION: 130..786
    ( D ) OTHER INFORMATION: /product="Truncated Tissue Factor"

( x i ) SEQUENCE DESCRIPTION: SEQ ID NO:5:

```
CGTTCCGCTC GATCTCGCCG CCAACTGGTA GAC ATG GAG ACC CCT GCC TGG CCC          54
                                    Met Glu Thr Pro Ala Trp Pro
                                    -32           -30

CGG GTC CCG CGC CCC GAG ACC GCC GTC GCT CGG ACG CTC CTG CTC GGC          102
Arg Val Pro Arg Pro Glu Thr Ala Val Ala Arg Thr Leu Leu Leu Gly
-25             -20                 -15                     -10

TGG GTC TTC GCC CAG GTG GCC GGC GCT TCA GGC ACT ACA AAT ACT GTG          150
Trp Val Phe Ala Gln Val Ala Gly Ala Ser Gly Thr Thr Asn Thr Val
                -5                  1               5

GCA GCA TAT AAT TTA ACT TGG AAA TCA ACT AAT TTC AAG ACA ATT TTG          198
Ala Ala Tyr Asn Leu Thr Trp Lys Ser Thr Asn Phe Lys Thr Ile Leu
            10                  15                  20

GAG TGG GAA CCC AAA CCC GTC AAT CAA GTC TAC ACT GTT CAA ATA AGC          246
Glu Trp Glu Pro Lys Pro Val Asn Gln Val Tyr Thr Val Gln Ile Ser
    25                  30                  35

ACT AAG TCA GGA GAT TGG AAA AGC AAA TGC TTT TAC ACA ACA GAC ACA          294
Thr Lys Ser Gly Asp Trp Lys Ser Lys Cys Phe Tyr Thr Thr Asp Thr
40                  45                  50                  55

GAG TGT GAC CTC ACC GAC GAG ATT GTG AAG GAT GTG AAG CAG ACG TAC          342
Glu Cys Asp Leu Thr Asp Glu Ile Val Lys Asp Val Lys Gln Thr Tyr
                60                  65                  70

TTG GCA CGG GTC TTC TCC TAC CCG GCA GGG AAT GTG GAG AGC ACC GGT          390
Leu Ala Arg Val Phe Ser Tyr Pro Ala Gly Asn Val Glu Ser Thr Gly
                75                  80                  85

TCT GCT GGG GAG CCT CTG TAT GAG AAC TCC CCA GAG TTC ACA CCT TAC          438
Ser Ala Gly Glu Pro Leu Tyr Glu Asn Ser Pro Glu Phe Thr Pro Tyr
        90                  95                  100

CTG GAG ACA AAC CTC GGA CAG CCA ACA ATT CAG AGT TTT GAA CAG GTG          486
Leu Glu Thr Asn Leu Gly Gln Pro Thr Ile Gln Ser Phe Glu Gln Val
105                 110                 115

GGA ACA AAA GTG AAT GTG ACC GTA GAA GAT GAA CGG ACT TTA GTC AGA          534
Gly Thr Lys Val Asn Val Thr Val Glu Asp Glu Arg Thr Leu Val Arg
120                 125                 130                 135

AGG AAC AAC ACT TTC CTA AGC CTC CGG GAT GTT TTT GGC AAG GAC TTA          582
Arg Asn Asn Thr Phe Leu Ser Leu Arg Asp Val Phe Gly Lys Asp Leu
                140                 145                 150

ATT TAT ACA CTT TAT TAT TGG AAA TCT TCA AGT TCA GGA AAG AAA ACA          630
Ile Tyr Thr Leu Tyr Tyr Trp Lys Ser Ser Ser Ser Gly Lys Lys Thr
            155                 160                 165

GCC AAA ACA AAC ACT AAT GAG TTT TTG ATT GAT GTG GAT AAA GGA GAA          678
Ala Lys Thr Asn Thr Asn Glu Phe Leu Ile Asp Val Asp Lys Gly Glu
        170                 175                 180

AAC TAC TGT TTC AGT GTT CAA GCA GTG ATT CCC TCC CGA ACA GTT AAC          726
Asn Tyr Cys Phe Ser Val Gln Ala Val Ile Pro Ser Arg Thr Val Asn
    185                 190                 195

CGG AAG AGT ACA GAC AGC CCG GTA GAG TGT ATG GGC CAG GAG AAA GGG          774
Arg Lys Ser Thr Asp Ser Pro Val Glu Cys Met Gly Gln Glu Lys Gly
200                 205                 210                 215

GAA TTT AGA GAA TAAGAATTC                                                795
Glu Phe Arg Glu
```

( 2 ) INFORMATION FOR SEQ ID NO:6:

( i ) SEQUENCE CHARACTERISTICS:
        ( A ) LENGTH: 251 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met   Glu   Thr   Pro   Ala   Trp   Pro   Arg   Val   Pro   Arg   Pro   Glu   Thr   Ala   Val
-32         -30                           -25                           -20

Ala   Arg   Thr   Leu   Leu   Leu   Gly   Trp   Val   Phe   Ala   Gln   Val   Ala   Gly   Ala
      -15                     -10                                -5

Ser   Gly   Thr   Thr   Asn   Thr   Val   Ala   Ala   Tyr   Asn   Leu   Thr   Trp   Lys   Ser
 1                      5                            10                              15

Thr   Asn   Phe   Lys   Thr   Ile   Leu   Glu   Trp   Glu   Pro   Lys   Pro   Val   Asn   Gln
                  20                        25                              30

Val   Tyr   Thr   Val   Gln   Ile   Ser   Thr   Lys   Ser   Gly   Asp   Trp   Lys   Ser   Lys
            35                              40                        45

Cys   Phe   Tyr   Thr   Thr   Asp   Thr   Glu   Cys   Asp   Leu   Thr   Asp   Glu   Ile   Val
      50                        55                              60

Lys   Asp   Val   Lys   Gln   Thr   Tyr   Leu   Ala   Arg   Val   Phe   Ser   Tyr   Pro   Ala
 65                     70                              75                              80

Gly   Asn   Val   Glu   Ser   Thr   Gly   Ser   Ala   Gly   Glu   Pro   Leu   Tyr   Glu   Asn
                        85                        90                              95

Ser   Pro   Glu   Phe   Thr   Pro   Tyr   Leu   Glu   Thr   Asn   Leu   Gly   Gln   Pro   Thr
                  100                       105                             110

Ile   Gln   Ser   Phe   Glu   Gln   Val   Gly   Thr   Lys   Val   Asn   Val   Thr   Val   Glu
            115                         120                       125

Asp   Glu   Arg   Thr   Leu   Val   Arg   Arg   Asn   Asn   Thr   Phe   Leu   Ser   Leu   Arg
      130                       135                         140

Asp   Val   Phe   Gly   Lys   Asp   Leu   Ile   Tyr   Thr   Leu   Tyr   Tyr   Trp   Lys   Ser
145                         150                         155                             160

Ser   Ser   Ser   Gly   Lys   Lys   Thr   Ala   Lys   Thr   Asn   Thr   Asn   Glu   Phe   Leu
                        165                         170                           175

Ile   Asp   Val   Asp   Lys   Gly   Glu   Asn   Tyr   Cys   Phe   Ser   Val   Gln   Ala   Val
                  180                       185                             190

Ile   Pro   Ser   Arg   Thr   Val   Asn   Arg   Lys   Ser   Thr   Asp   Ser   Pro   Val   Glu
            195                       200                         205

Cys   Met   Gly   Gln   Glu   Lys   Gly   Glu   Phe   Arg   Glu
      210                       215
```

QUANTITATIVE CLOTTING ASSAY FOR ACTIVATED FACTOR VII

RELATED APPLICATION DATA

This application is a continuation-in-part of U.S. patent application Ser. No. 07/683,682, filed Apr. 10, 1991, U.S. Pat. No. 5,472,850. +gi The U.S. government has rights in this invention by virtue of a grant from the National Institutes of Health.

TECHNICAL FIELD

This invention relates to the field of detection of blood factors involved in blood coagulation.

BACKGROUND OF THE INVENTION

Blood coagulation results from the production of thrombin, a proteolytic enzyme inducing platelet aggregation and cleaving fibrinogen to fibrin, which stabilizes the platelet plug. A number of proenzymes and procofactors circulating in the blood interact in this process through several stages during which they are sequentially or simultaneously converted to the activated form, ultimately resulting in the activation of prothrombin to thrombin by activated factor X (fXa) in the presence of factor Va, ionic calcium, and platelets.

Factor X can be activated by either of two pathways, termed the extrinsic and intrinsic pathways. The intrinsic pathway, or surface-mediated activation pathway, consists of a series of reactions where a protein precursor is cleaved to form an active protease, beginning with activation of factor XII to factor XIIa, which converts factor XI to factor XIa, which, in the presence of calcium, converts factor IX to factor IXa. Factor IX can also be activated via the extrinsic pathway by tissue factor (TF) in combination with activated factor VII (factor VIIa; fVIIa). The activated factor IX, in the presence of calcium, phospholipid (platelets), and factor VIIIa, activates factor X to factor Xa.

Physiologically, the major pathway involved in coagulation is believed to be the extrinsic pathway, an essential step of which is activation of factor VII to factor VIIa. Clotting assays (and other activity assays) designed to measure factor VII and VIIa generally must employ TF, the cofactor required for factor VIIa coagulant activity. Most commonly, TF is provided as a relatively crude preparation known as thromboplastin. Tissue factor is an integral membrane glycoprotein having a protein and a phospholipid component. It has been isolated from a variety of tissues and species and reported to have a molecular mass of between 42,000 and 53,000. The original crude tissue abstracts referred to the fraction containing the tissue factor as thromboplastin. DNA encoding tissue factor and methods for expression of the protein have now been reported, for example, in European Patent Application 0 278 776 by Genentech, Inc. and by J. H. Morrissey, et al., "Molecular cloning of the cDNA for tissue factor, the cellular receptor for the initiation of the coagulation protease cascade," Cell 50:129–135 (1987).

The complex of factor VIIa and TF is the most potent known trigger of the clotting cascade. Factor VII is present in plasma at a concentration of about 0.5 µg/ml plasma. In contrast, measured as described herein, factor VIIa is present in plasma at trace levels of about 0.5 to 8.4 ng/ml. Accordingly, factor VII is normally in considerable excess over factor VIIa. As there are presently no immunoassays capable of discriminating between factor VII and VIIa, current assays attempt to exploit the difference in enzymatic activity between the two, relative to total factor VII protein.

Factor VIIa circulates with a relatively long half-life of about two hours in plasma. This is an unusual property among activated coagulation enzymes, which typically are inactivated very rapidly by various protease inhibitors in plasma. Some studies have suggested that elevated levels of plasma factor VIIa are associated with increased risk of thromboembolic disease. This may be due to a direct effect of factor VIIa in promoting thrombosis, or because elevated plasma factor VIIa is a by-product of a "prethrombotic state". In either case, there is clinical interest in measuring plasma factor VIIa levels.

Two basic types of assays are routinely employed to assess coagulation function: clotting assays and chromogenic substrate assays. Clotting assays compare clotting times relative to normal controls (time in seconds to clot formation versus percent normal control, also referred to as one unit). Chromogenic substrate assays are typically used only with the purified enzymes and the amount of active factor calculated based on the amount of product generated in a given time as determined by absorbance of light transmitted through the sample at a particular wavelength. Immunological assays involving antigen-antibody reactions are also sometimes used to measure the total amount of protein present.

Prothrombin time (PT) and activated partial thromboplastin time (aPTT) assays are routinely employed clinically in the assessment of hemostatic function. PT is performed by adding a preparation of phospholipid, tissue factor and calcium to the patient's citrated plasma and determining the time required for a clot to form. This test measures the aggregate activity of factors II, VII, X, V and fibrinogen. The PT is often used to follow oral anticoagulant therapies, i.e., coumarin and other anti-vitamin K drugs. The aPTT test is performed by adding a preparation of celite (or other contact activator), phospholipid, and calcium to the patient's citrated plasma and determining the time required for a clot to form. This test measures the aggregate activity of factors XII, XI, IX, VIII, X, II, V and fibrinogen. The aPTT is commonly used as a coagulation screening test for factor dysfunction in hospitalized patients.

In contrast to these general assays, quantitative assays of specific individual coagulation factors are usually performed using a plasma deficient in the factor to be assayed and comparing clotting times relative to controls. Typically, the amount of factor VII/factor VIIa present in a patient's plasma would be determined using factor VII deficient plasma, adding a dilution of patient plasma, TF, and calcium, usually in the form of calcium chloride, and determining the time required for the plasma mixture to clot. The result is a measure of what is called "factor VII coagulant activity", or FVIIc. In reality, FVIIC is a function of the concentrations of both factor VII and VIIa. It is difficult to assess the amount of factor VII relative to the amount of factor VIIa, however, since TF greatly accelerates the activation of factor VII, and the newly converted factor VIIa contributes to the measured activity. A further complication of the significance of FVIIc is the recent finding of an unusual, lipoprotein-associated form of factor VII that has elevated FVIIC activity. The nature of this lipoprotein-associated form of factor VII is poorly understood at the present time.

These factors limit the sensitivity of existing assays and complicate their interpretation. In conventional clotting assays, human factor VIIa has approximately 25-fold more activity than factor VII on an equimolar basis. This means that prior assays have had difficulty detecting concentrations of factor VIIa protein that are much below 1/25 of the concentration of factor VII. The normal plasma concentration of factor VII is approximately 0.5 µg/ml, and the lower limit of detection of factor VIIa in normal plasma using the conventional factor VII clotting assay is between 1 and 10 ng/ml.

In order to try to control for possible variation of plasma factor VII levels, another assay is usually performed in parallel that is designed to measure total factor VII plus VIIa. This can be an immunoassay or a chromogenic substrate assay in which factor VII is converted to factor VIIa. The final result is then expressed as a ratio of factor VII clotting activity (FVIIc) to total factor VII, and an increase in the ratio above normal is taken as evidence of an increased level of factor VIIa in the test plasma. These assays do not really measure factor VIIa directly and specifically, nonetheless, nor do these assays give a measure of absolute level of factor VIIa. It is thought that elevated FVIIc can be due to the presence of elevated circulating factor VIIa levels. Alternatively, elevated FVIIc can be due to an increased concentration of factor VII in plasma. In any case, the results from conventional assays of FVIIc depend heavily on the source of thromboplastin, as reported by Poggio, et al., "Factor VII clotting assay: influence of different thromboplastins and Factor VII-deficient plasmas," *Thrombosis Haemostasis*, 65:160–164 (1991), making it difficult to compare the results of such assays from one laboratory with another.

In summary, prior art methods for measuring factor VIIa levels in plasma are limited by the interference of factor VII which is also present in plasma. There are therefore three main drawbacks to the available assays: (1) it: is extremely difficult to measure absolute levels of factor VIIa in plasma, as compared with levels of factor VII; (2) low sensitivity of available assays means that only factor VIIa levels substantially increased over normal can be measured; and (3) it is difficult to directly compare the results obtained in different studies.

It is therefore an object of the present invention to provide a sensitive assay which measures the absolute levels of factor VIIa, not factor VII, in plasma.

It is further object of the present invention to provide an assay for factor VIIa which is reproducible and commercially viable and can be performed with existing methodologies and most reagents, manually or automatically.

SUMMARY OF THE INVENTION

An in vitro assay for detecting and quantitating factor VIIa (the activated form of coagulation factor VII) in human plasma has been developed. The single-stage clotting assay is performed in a manner nearly identical to the prothrombin time (PT) clotting assay using a small sample of blood drawn into a citrate anticoagulant, from which plasma is prepared by centrifugation. A modified clotting assay is then performed on a sample of the plasma using a preparation of truncated tissue factor and phospholipid vesicles in place of thromboplastin. The truncated derivative of tissue factor retains cofactor activity toward factor VIIa, but, unlike normal tissue factor, does not stimulate the conversion of factor VII to factor VIIa. As a result, unactivated factor VII, which is also present in plasma, does not interfere with the assay. The clotting time obtained in this assay is directly related to the level of plasma factor VIIa and is quantitated by comparison to a standard curve generated using factor-VII deficient plasma supplemented with known quantities of factor VIIa. The useful range of the assay is 10 pg factor VIIa/ml to 10 µg factor VIIa/ml in plasma. The lower limit of detection of factor VIIa in the truncated tissue factor-based assay is calculated to be less than 10 pg factor VIIa/ml.

The assay is useful in accurately measuring plasma levels of factor VIIa in individuals. Recent studies have indicated a possible correlation between elevated factor VIIa levels and the risk of such disorders as ischemic heart disease and fetal growth retardation. The assay can also be used to monitor factor VIIa therapy in hemophiliacs and other individuals undergoing factor VIIa therapy.

BRIEF DESCRIPTION OF THE DRAWINGS

FIG. 1 is the amino acid and nucleotide sequence encoding a soluble form of truncated tissue factor (tTF). Nucleotide sequence is numbered on the left. Amino acid sequence is given above the nucleotide sequence using the standard one-letter code. The signal peptide is underlined.

DETAILED DESCRIPTION OF THE INVENTION

Figure 2:
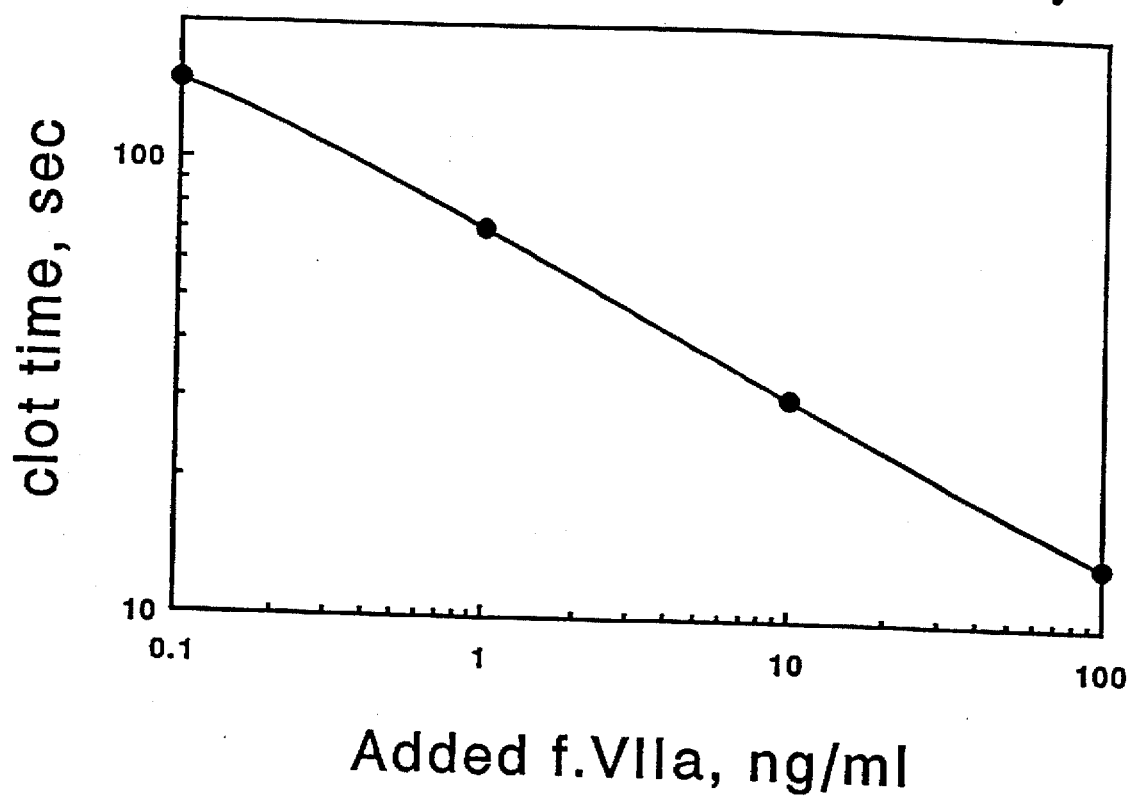
FIG. 2 is an exemplary factor VIIa standard curve generated using an automated coagulometer (ACL™ 300 Automated Coagulation Laboratory) run in the PT mode, using a high-sensitivity tTF reagent. Human factor VII-deficient plasma was supplemented with varying concentrations of recombinant human factor VIIa spanning the anticipated normal range of FVIIa concentrations. The tTF reagent contained 1 µM tTF. Data (clotting times vs. added factor VIIa concentration) were plotted on log-log axes and fit to a fourth order polynomial by regression analysis.

Clotting of citrate-anticoagulated, platelet-poor plasma is initiated by a combination of truncated tissue factor, phospholipid vesicles and calcium ions. The clotting time is an indicator of the level of factor VIIa present in the plasma.

There are two preferred embodiments of the assay for activated factor VII: a manual version, using a relatively low concentration of phospholipids, and an assay for use in automated coagulometers and fibrometers, which most clinical labs in the U.S. are using. The manual assay can be manipulated to have a million-fold range in sensitivity, ranging from 10 pg/ml to 10 µg/ml. This is not practical using the automated coagulometers due to small but significant reagent carry-over. Accordingly, two "stock" solutions of the tTF reagent, containing different amounts of tTF and/or phospholipid, are maintained: one, for measuring the normal range of fVIIa levels, approximately 0.1 to 10 ng/ml, and a second for measuring the therapeutic range of fVIIa levels, up to about 4 μg/ml.

Reagents for use in Activated factor VII assays.

The reagents common to all embodiments of the assay are the plasma sample, a source of phospholipid, a source of clotting factors other than factor VIIa, truncated tissue factor (tTF), and calcium.

1. Phospholipid Vesicles.

In the preferred embodiment, the formulation consists of 1 μM truncated tissue factor reagent (25.5 μg/ml) plus 80 μg mixed brain phospholipid vesicles/ml suspended in TBS/BSA (50 mM Tris.HCl pH 7.4, 100 mM NaCl, 0.02% sodium azide, 0.1% bovine serum albumin). Phospholipid vesicles (600 μM) can be prepared by the deoxycholate method of Carson and Konigsberg, *Thrombosis Haemostasis* 44:12–15 (1981). Phospholipid vesicles are not absolutely required, but their addition increases the sensitivity of the assay. It is believed that the presence of the vesicles decreases variability in the assay, since coagulation is less dependent on the residual content of lipoprotein particles, platelets and cell membrane fragments in the plasma samples.

Cephalin, prepared according to Bell and Alton, *Nature, London*, 174:880–881 (1954), the teachings of which are incorporated herein, and available commercially from a number of suppliers, including, for example, Rabbit Brain Cephalin from Sigma Chemical Company, St. Louis, Mo., can also be used as the source of phospholipid vesicles. The vesicle preparations are reconstituted according to the manufacturer's instructions and employed at the final concentration recommended for use in the partial thromboplastin time (PTT) assay, described by Langdell, et al., *J Lab Clin Med* 41:637 (1953).

Other preparations of phospholipid vesicles suitable for use as a "platelet substitute" in PTT assays or thrombin generation time (TGT) assays are acceptable for use in the truncated TF assay for factor VIIa, including vesicles prepared from crude phospholipid extracts of tissues as well as vesicles prepared from purified or synthetic phospholipids. Such vesicle preparations must not contain tissue factor or additives that activate the contact pathway of coagulation. Examples of unsuitable preparations of vesicles are commercial thromboplastins designed for use in PT assays and "activated partial thromboplastins", cephalin preparations admixed with activating agents such as elegiac acid, kaolin, or venom extracts.

2. The tTF Reagent.

As used herein, "truncated tissue factor" or "tTF" is a soluble tissue factor having an extracellular domain which is not bound to a phospholipid membrane surface and therefore does not support conversion of fVII to fVIIa.

An appropriate truncated tissue factor is a modified tissue factor, which lacks sufficient amino acids from the transmembrane domain, which normally function to bind to phospholipid membranes, so that the truncated tissue factor does not have that binding capability. Binding tests can be performed to ascertain if a particular tTF is suitable for use in the invention. There are various techniques known in the art for testing for binding. One method for measuring the binding of proteins to phospholipid vesicles is by quantification of the increase in light scattering, as has been employed previously for coagulation proteins by G. L. Nelsestuen et al., "Interaction of vitamin K dependent proteins with membranes", *Biochemistry*, 17:2134–2138 (1978). Truncated forms of tissue factor which do not have detectable binding affinity for phospholipid vesicles by this or other such methods would be suitable for use in the invention.

Preferably, the truncated tissue factor has a sequence which differs from Tissue Factor by omitting one or more of the amino acids from number 209 to number 263 of SEQ ID NO:2. More preferably, the tTF useful in the invention will have a sequence of 1 to about 209–222 of SEQ ID NO:2; still more preferably a sequence of 1 to about 218–220 of SEQ ID NO:2; and most preferable a sequence of 1 to 219 of SEQ ID NO:2.

Portions of full length tissue factor (SEQ ID NO:2) can be used. It is believed that a protein having the amino acid sequence from about 1–2 to about 209–210 would constitute the minimum functional length, since this would include the last disulfide bond needed for tissue factor function found at position 209. The protein can be conveniently truncated near 209. For example, position 210 (methionine) can be cleaved by cyanogen bromide treatment.

Variations on tTF which contain truncations at the C-terminal end of varying lengths can be used in the invention. This includes tTF consisting of the sequence 1–219 of tissue factor as described above. Another example of a form of tTF suitable for the invention consists of the sequence 1–218 as described by E. Waxman et al., "Tissue factor and its extracellular soluble domain: the relationship between intermolecular association with Factor VIIa and enzymatic activity of the complex", *Biochemistry*, 31:3998–4003 (1992). Yet another example of a form of tTF suitable for the invention consists of the sequence 1–217 of tissue factor as described by Y. Shigematsu et al., "Expression of human soluble tissue factor in yeast and enzymatic properties of its complex with Factor VIIa", *Journal of Biological Chemistry*, 267:21329–21337 (1992).

Variations on tTF which contain truncations or additions at the N-terminus of the protein can be used in the invention. For example, a variant of tTF which also lacks the first amino acid (sequence 2–219 of tissue factor) has been described by A. R. Rezaie et al., "Expression and purification of a soluble tissue factor fusion protein with an epitope for an unusual calcium-dependent antibody", *Protein Expression and Purification*, 3:453–460 (1992). This form of tTF is suitable for use in the invention. Another example of a tTF variant is one that consists of the sequence 2–219 of tissue factor plus an eighteen amino acid-long extension of unrelated sequence at the N-terminus, as reported by Rezaie et al. (ibid). This variant is also suitable for use in the invention.

In the preferred embodiment, truncated tissue factor is a recombinant protein produced in vitro in cell culture using a human cell line (293 cells), ATCC CRL 1573. These cells are stably transfected with a mutant form of the human tissue factor cDNA carried in a commercially available expression vector, and secrete a form of tissue factor consisting only of amino acids 1–219 (numbered according to Morrissey, et al., *Cell* 50:129–135 (1987), the teachings of which are incorporated herein).

The recombinant, truncated tissue factor is purified from the culture medium using an immobilized monoclonal antibody to human tissue factor, such as TF9-5B7, described in Morrissey, et al., "Monoclonal antibody analysis of purified and cell-associated tissue factor,"*Thrombosis Research* 52:247–261 (1988). Hybridomas for production of monoclonal antibodies can be propagated by ascites growth and the monoclonal antibodies (MAbs) purified from ascites fluid using the BioRad MAPS II system for MAb purification, as described by Morrissey, et al., *Thrombosis Research* 52:247–261 (1988).

The TF9-5B7 is coupled to Affigel™ beads. Detergent is not used during the purification of $TF_{219}$. After removal of cellular debris by centrifugation, the culture medium is made 25 mM in Tris.HCl (pH 7.4), 10 mM in sodium EDTA (pH 7.4), and 0.1% in sodium azide by the addition of concentrated stock solutions. In order to remove proteins that bind to agarose beads non-specifically, the culture medium is gently agitated for 4 hr at 4° C. with AffiGel™ –10 beads that had previously been blocked chemically with glycine ethyl ester (GEE-AffiGel™). The GEE-AffiGel™ beads are removed by filtration through a sintered glass funnel, and the supernatant is agitated overnight at 4° C. with the MAb TF9-5B7 coupled to AffiGel™ beads (typically 2 ml of beads). The TF9-5B7-AffiGel™ beads are collected on a sintered glass funnel, and the beads are washed on the funnel with 100 ml of TBS-EDTA (TBS=100 mM NaCl, 50 mM Tris.HCl pH 7.4, 0.02% sodium azide; TBS-EDTA TBS with 10 mM EDTA included). The beads are then transferred to a chromatography column and washed with 40 ml TBS followed by 40 ml of a solution consisting of 1M NaCl, 10 mM Tris.HCl pH 7.4, 0.02% sodium azide. Truncated tissue factor is eluted from the beads using 100 mM glycine.HCl pH 2.5, with 1 ml fractions being collected into tubes containing 57 µl 1M Tris base (to immediately neutralize the acidic glycine buffer). Fractions containing protein are detected using the BCA protein assay (Pierce), pooled, dialyzed against TBS, and then stored at –70° C. Protein concentrations are determined using standard methods such as the BCA assay (Pierce Chemical Co.) based on a bovine serum albumin standard of known concentration.

The $TF_{1-219}$ deletion mutant used in the preferred embodiment was constructed and stably expressed in eukaryotic cells as follows. A deletion mutant of human TF cDNA was created that contained the coding sequence for the predicted leader peptide and extracellular domains, but lacked the predicted transmembrane and cytoplasmic domains. Starting with clone pCTF543 (described by Mackman et al., *Biochemistry* 28:1755–1762 (1989)), a 775 bp fragment of TF cDNA was released by digestion with EcoRI. This fragment extended from the 5' noncoding sequence to the EcoRI site in the coding sequence (nucleotides 1 through 775 as numbered according to Morrissey et al., *Cell* 50:129–135 (1987)). To each end of the 775 bp cDNA fragment was ligated a double-stranded synthetic oligonucleotide made by annealing together the following two single-stranded oligonucleotides (sequences listed 5' to 3'): AATTTAGAGAATAAGAATTCGGG (SEQ ID NO:3) and CCCGAATTCTTATTCTCTA (SEQ ID NO:4). On the 3' end of the insert, the adaptor took advantage of redundancy in the codon for phenylalanine by changing the codon for $Phe^{217}$ from TTC to TTT, thereby destroying the original EcoRI site but preserving the encoded amino acid sequence through $Glu^{219}$. The codon for $Ile^{220}$ was replaced with a TAA stop codon, and a new EcoRI site was generated at the 3' end for cloning purposes. Amino acid 219 is the last amino acid upstream of the predicted transmembrane domain, so this construct encodes the whole extracellular domain of TF (referred to here as $rTF_{1-219}$). The double-stranded oligonucleotide was also ligated to the 5' end of the clone, but as it has no initiator ATG codon, it is predicted to have no effect on expression of the recombinant protein.

The resulting 805 bp $TF_{1-219}$ cDNA was digested with EcoRI and subcloned into the EcoRI site of the mammalian expression vector pCDNAI (available from Invitrogen, San Diego, Calif.) in the proper orientation for expression. The resulting construct was introduced into 293 cells by liposome-mediated transfection using Lipofectin Reagent (available from Gibco/BRL, Gaithersburg, Md., and used according to the manufacturer's directions). Stable clones were selected by co-transfection of the construct with the plasmid pMAM-neo (available from Clontech, San Francisco, Calif.) in a 10:1 molar ratio. Stably transfected cell lines expressing truncated TF were selected initially by treating the cells with the neomycin analog G418 (Geneticin from Gibco/BRL, Gaithersburg, Md.) at 400 µg/ml. Subsequently, culture supernatants of surviving drug-resistant colonies were screened for high levels of expression of truncated TF using a two-site, sandwich, enzyme-linked immunoassay based on two MAbs described by Morrissey, et al., *Thrombosis Research* 52:247–261 (1988). One stable, clonally-derived cell line was chosen that secreted truncated TF at levels of up to 1 mg per liter per day in roller bottle culture.

For production of recombinant truncated TF, cells are typically grown to confluence in roller bottles in Dulbecco's Modified Eagle's Medium (DMEM) supplemented with 10% iron-supplemented calf serum (HyClone Laboratories, Logan, Utah). Upon reaching confluence, the cultures are shifted to DMEM containing 2% serum, and culture medium is collected every four days thereafter.

The nucleotide and amino acid sequence of the preferred truncated tissue factor (tTF) is shown in FIG. 1 and in SEQ ID NO:5 and SEQ ID NO:6, respectively. The truncated tissue factor protein lacks the predicted transmembrane and cytoplasmic domains of tissue factor. This version of the protein retains cofactor activity, as reported by Ruf, et al., "The isolated extracellular domain of tissue factor is functional on phospholipid surfaces," *Thrombosis & Haemostasis* 62:347 (abstract) (1989) and Ruf, et al., "Phospholipid-independent and -dependent interactions required for tissue factor receptor and cofactor function," *J Biol Chem* 266:2158–2166 (1991). However, it has now been discovered that this truncated form of tissue factor fails to support conversion of factor VII to VIIa, allowing it to be used in a specific clotting assay for factor VIIa free from interference by factor VII.

Other suitable modified tissue factors would have slight variations from the protein shown in SEQ ID NO:6, as is illustrated by modifying full length tissue factor of SEQ ID NO:2 in the region between amino acid 209 and 263. The transmembrane domain allowing tissue factor to bind to phospholipid membrane is in the region of about 218 or 219 to 242. While the studies have not been done to determine exactly how many of the transmembrane amino acids can be added to the preferred 1–219 embodiment of SEQ ID NO:6 without changing its function in the assay, given the disclosure of this invention, it is believed to be a matter of routine experimentation. In addition, fewer than 219 amino acids may result in a truncated tissue factor equally useful in the present assay. While determining how few are required is a matter of routine now that the present assay has been disclosed, it can be appreciated that such experimentation would not be necessary given the proven utility of SEQ ID NO:6.

The essential difference between truncated tissue factor and wild-type tissue factor is that truncated tissue factor is no longer tethered to the phospholipid membrane surface. It is therefore expected that other methods for preparing truncated tissue factor can be used to generate a soluble form of tissue factor that retains some cofactor activity while no longer stimulating conversion of factor VII to factor VIIa. Methods include enzymatic digestion of wild-type tissue factor to separate the predicted extracellular domain from the transmembrane region. Recombinant human TF is available from Calbiochem. Precise positioning of the stop codon following amino acid 219 is believed to not be essential to make functional truncated TF, and other placements of a stop codon near amino acid 219 are predicted to yield an equivalent product with respect to its utility in the factor VIIa assay described herein. It is predicted that truncated tissue factors having a sequence from 1 to 209–222 of SEQ ID NO:2 would be functional in the assay, and perhaps other truncated tissue factors modified in length and by attachment of substituent groups, as long as the functions are similar to the preferred tTF: lack of binding to phospholipid membranes, retention of cofactor activity while no longer stimulating conversion of factor VII to factor VIIa.

A factor VIIa standard curve must be generated for each new batch of tTF reagent, and the curve is applicable only for the assay configuration tested (e.g., for the specific manner of performing the manual tilt-tube method, or for the specific automated or semi-automated coagulation measuring device used to generate the standard curve). Changing from one measuring device to another, or changing batches of tTF reagent, will necessitate generating a new standard curve.

3. Purified Proteins and Deficient Plasmas

Factor VII can be prepared as described by Fair, Daryl S., "Quantitation of Factor VII in the plasma of normal and Warfarin-treated individuals by radioimmunoassay," *Blood* 62:784–791 (1983). FVII can be converted to fVIIa by incubation of the purified protein with factor Xa immobilized on Affi-Gel™ 15 beads (Bio-Rad). Conversion can be monitored by SDS-polyacrylamide gel electrophoresis of reduced samples. Free factor Xa in the fVIIa preparation can be detected with the chromogenic substrate methoxycarbonyl-D-cyclohexylglycyl-glycyl-arginine-p-nitroanilide acetate (Spectrozyme™ FXa, American Diagnostica, Greenwich, Conn.) at 0.2 mM final concentration in the presence of 50 mM EDTA. Recombinant fVIIa can also be purchased from Novo Biolabs (Danbury, Conn.) or from Celsus Laboratories (Cincinnati, Ohio).

In the preferred embodiment, test plasma consists of platelet-poor, citrated plasma, although other anticoagulants can be used such as ethylenediamine tetracetic acid (EDTA) or sodium or potassium oxalate, and platelets do not have to be removed. This is prepared using standard hematologic techniques by drawing a small sample of blood by venipuncture into a citrate anticoagulant (ACD or CPD), from which plasma is prepared by centrifugation.

In the preferred embodiment, the reference plasmas from which the calibration standard curve is generated consist of known quantities of purified, recombinant human factor VIIa added to human factor VII-deficient plasma. The human factor VII-deficient plasma can be from congenitally deficient donors (available from George King Biomedical, Overland Park, Kans.) or can be immunodepleted plasma (available from American Diagnostica, Greenwich, Conn.). Concentrations of added factor VIIa range from 1 pg/ml to 10 µg/ml. A log-log plot of clotting time vs. factor VIIa concentration is prepared and a curve (4th order polynomial) is fit using regression analysis. Clotting times for unknown plasma samples are converted to factor VIIa concentrations using graphical analysis or a computer program.

Values obtained using the preferred embodiment of this assay for plasma levels of factor VIIa range from 0.5 to 8.4 ng/ml.

The plasma must be handled and stored in containers made of materials known not to promote activation of the contact system of coagulation. This includes the materials the plasma comes in contact with during the assay. The manual assay typically employs tubes formed of plastics such as polystyrene, polyethylene and polypropylene. An example of an unacceptable material is untreated glass, well-known for its ability to activate the contact coagulation system. Glass treated by siliconization, or by other methods known to eliminate contact activation of plasma, are also acceptable.

4. Ionic calcium

Typically, ionic calcium is provided as a 25 mM solution of $CaCl_2$. Calcium chloride is available from a number of commercial sources.

Assays for activated factor VII using the tTF

The assay can be performed using the reagents described above and obtained individually, or as a kit to be used in clinical coagulation laboratories, alone or in combination with other assays such as antigen-antibody assays. The essential components of the kit are the truncated tissue factor reagent and a factor VIIa standard to be diluted with factor VII-deficient (or factor VII-depleted) human plasma or a set of factor VIIa standards consisting of factor VII-deficient (or factor VII-depleted) human plasma supplemented with known concentrations of factor VIIa. In most cases, the kit would be used with existing equipment such as coagulometers. Since the assay is conducted in a manner similar to that for the PT assay, minimal training of personnel is required.

It is also preferred that a kit contain instruction for performing the assay, which instructions would be printed on a package insert or packaging included in the kit. The printed matter can also be included on receptacles or tubes included in the kit, and indicia of sample and reagent volumes can be indicated in the test receptacle. The precise instructions would vary depending on whether a manual or automated method is used, but would include instructions for dilution of the kit components and/or the plasma sample, volume of reagent to add to each test, volume of plasma sample to add to each test, amount of calcium kit component or alternatively amount and concentration of calcium ion solution to add to the test, preferred temperature conditions, and timing of reagent addition, and use of standard fVIIa to calibrate test results.

The sensitivity of the tTF reagent to factor VIIa levels, expressed as the decrease in clotting time of factor VIIa-containing plasma when assayed in the presence versus the absence of tTF reagent, is a function of the concentrations of both tTF and phospholipid vesicles (cephalin). Therefore, the sensitivity of the reagent can be increased, i.e., the clotting time at a given factor VIIa concentration shortened, by increasing the concentration of tTF or cephalin in the reagent. Sensitivity of the reagent is adjusted by varying the concentrations of tTF or cephalin to achieve the desired range of clotting times relative to the range of factor VIIa levels to be measured. Preferably, the cephalin concentration is kept constant at the strength normally employed for PTT or TGT assays, and the sensitivity of the tTF reagent is adjusted by varying only the concentration of tTF.

Figure 3:
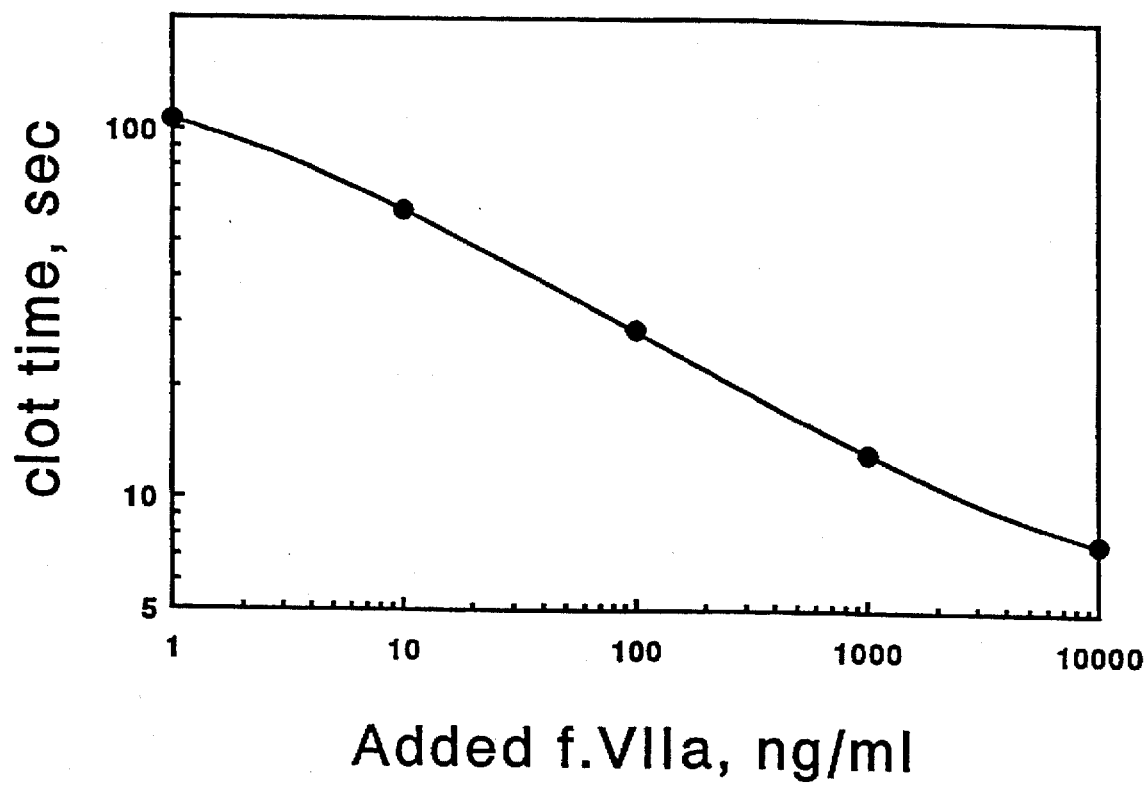
FIG. 3 is an exemplary plot of clotting times obtained in the tTF assay for factor VIIa with a low-sensitivity tTF reagent and normal human plasma supplemented with factor VIIa at levels that mimic the therapeutic range. The tTF reagent contained 50 nM tTF. Data (clotting times vs. added factor VIIa concentration) were plotted on log-log axes and fit to a fourth order polynomial by regression analysis.

For example, high sensitivity tTF reagents can be prepared using rabbit brain cephalin and between 100 µM and 1 µM tTF. As illustrated in FIG. 2, the high sensitivity reagent is most useful for manual, semi-automated, or automated detection of factor VIIa levels in the anticipated normal range (approximately 0.1 to 10 ng factor VIIa/ml). A low sensitivity tTF reagent can be prepared using rabbit brain cephalin and between 10 and 50 nM tTF. As illustrated in FIG. 3, the low sensitivity reagent is most useful for manual, semi-automated, or automated detection of factor VIIa levels in the therapeutic range, up to approximately 5 µg factor VIIa/ml.

1. Manual clotting assays

In the preferred embodiment, the manual assay is performed as follows:

1. Pre-warm 12×75 mm polystyrene test tubes to 37° C. in a water bath.
2. Add 0.1 ml truncated tissue factor reagent per tube and allow to warm to 37° C. for at least 3 min.
3. Add 0.1 ml test plasma, mix and warm for exactly 30 sec.
4. Add 0.1 ml pre-warmed (37° C.) 25 mM $CaCl_2$ solution, mix immediately, and determine clotting time from point of calcium addition using the manual tilt-tube method. The endpoint is when a visible clot is formed in the tube.

Figure 4:
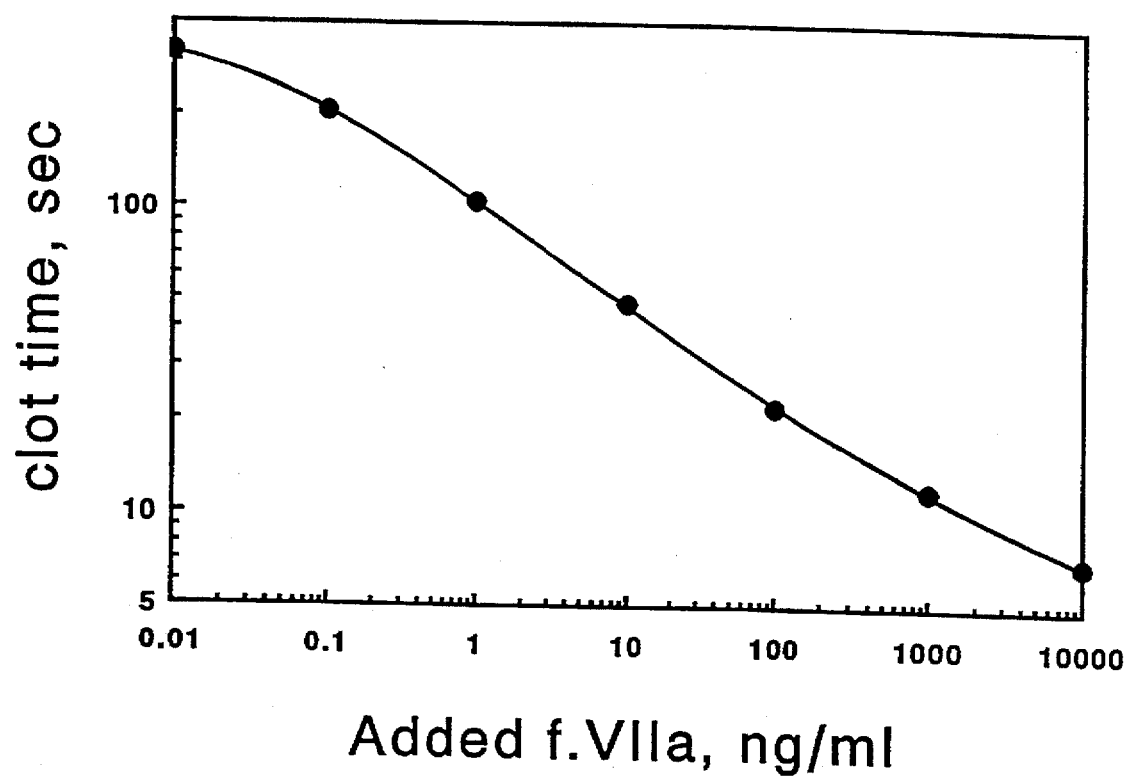
FIG. 4 is an exemplary factor VIIa standard curve generated by the manual tilt tube method and employing a high-sensitivity tTF reagent. Human factor VII-deficient plasma was supplemented with varying concentrations of recombinant human factor VIIa (spanning 10 pg/ml to 10 µg/ml fVIIa). The tTF reagent contained 100 nM tTF. Data (clotting times vs. added factor VIIa concentration) were plotted on log-log axes and fit to a fourth order polynomial by regression analysis.

FIG. 4 is a graph of a factor VIIa standard curve generated by the manual tilt tube method employing tTF.

Figure 5:
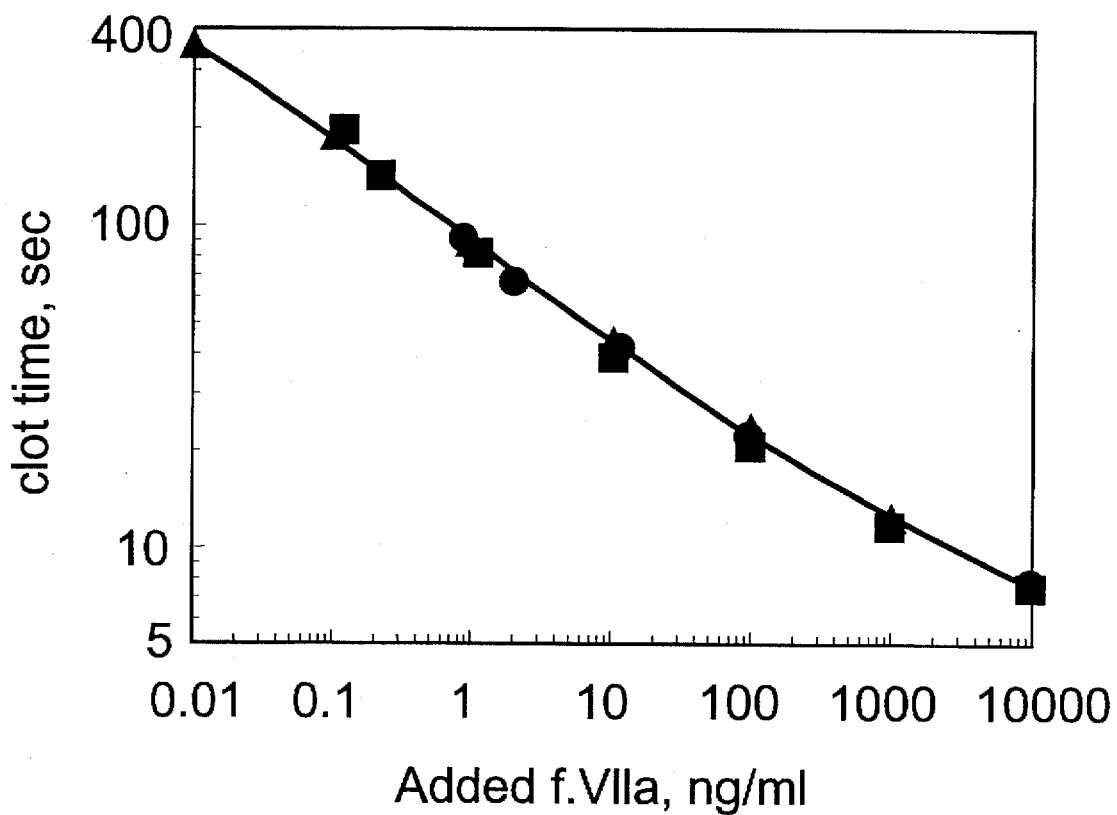
FIG. 5 is an exemplary factor VIIa assay of normal and hemophilic plasmas (containing endogenous FVII and FVIIa) generated by the manual tilt tube method and employing a high-sensitivity tTF reagent. Data (clotting times vs. added factor VIIa concentration) were replotted to remove endogenous FVIIa concentrations.

The manual tilt tube assay was performed with normal and hemophilic plasmas which contain both endogenous FVII and FVIIa. FIG. 5 is a graph depicting assay results replotted to remove endogenous FVIIa concentrations. The plots produced fit well to the standard curve obtained with FVII-deficient plasma, showing that the clotting assay is sensitive and specific in measuring FVIIa concentration in plasma, despite the endogenous FVII in normal and hemophilic plasmas.

The assay was also performed utilizing FVII-deficient plasma to which recombinant FVII containing a known amount of endogenous FVIIa was added. When the clotting times were compared to a FVIIa standard curve, the results corresponded to the amount of endogenous FVIIa present in the recombinant FVII. Thus, it was shown that significant amounts of zymogen FVII were not converted to FVIIa in the clotting assay and that zymogen FVII did not interfere in the measurement of FVIIa in the assay. (Neuenschwander, et al., "Deletion of the membrane-anchoring region of tissue factor abolishes autoactivation of factor VII, but not cofactor function: analysis of a mutant with a selective deficiency in activity." *J Biol Chem* 267:14477–14482 (1992))

2. Automated Measuring Devices for Coagulation Testing

Automated and semi-automated devices for coagulation testing are available from a variety of suppliers. An example of a fully automated, photometric-based detection instrument suitable for the tTF assay for factor VIIa is the ACL™ 300 Automated Coagulation Laboratory available from Instrument Laboratory Division of Fisher Scientific Co. (Lexington, Mass.). In principle, any device capable of determining prothrombin times can be used for the tTF assay for factor VIIa. This includes devices that detect clots photometrically (coagulometers) or using electrodes (fibrometers). The devices should be run in PT mode, and the data should be recorded in seconds. A variety of automated and semi-automated coagulation testing devices suitable for use with the tTF assay for factor VIIa are available from Scientific Products Division of Baxter Diagnostics, Inc. (McGaw Park, Ill.).

3. Application of tTF in Chromogenic Substrate Assays and Other Assay Configurations The tTF assay for plasma factor VIIa levels can be adapted for any assay configuration that employs TF or thromboplastin by substituting the tTF reagent for thromboplastin. The resulting assay will then be capable of measuring factor VIIa levels independent of the level of inactivated factor VII. An example of such an adaptation is substitution of tTF reagent for thromboplastin in the chromogenic substrate assay (also known as coupled amidolytic assay) for factor VII (FVIIam; see, for example, Seligsohn et al, "Coupled amidolytic assay for Factor VII: its use with a clotting assay to determine the activity state of Factor VII." *Blood* 52:978–988 (1978). Another example is substitution of tTF reagent for thromboplastin in alternative PT assays such as those performed on whole, citrated blood, for example, the Coumatrak™ Protime Test System marketed by Du Pont Company, Wilmington, Del.

4. tTF Assay for Factor VIIa Levels in Plasmas with Abnormal Prothrombin Times

The tTF clotting assay for plasma factor VIIa depends on adequate levels of factors II, V, X and fibrinogen. Deficiencies in any of these factors, or the presence of inhibitors of these factors in plasma, could result in inaccurate measurement of factor VIIa levels. Accordingly, plasma samples may be diluted ten-fold or one hundred-fold with factor VII deficient plasma. One way to determine if dilution is desirable is to run the tTF assay for factor VIIa levels in parallel with a standard PT assay, and plasmas that exhibit PT values outside the acceptable normal range would be diluted as described. The resulting value for plasma factor VIIa is then multiplied by the dilution factor to calculate the level of factor VIIa present in the original, undiluted plasma.

5. FVIIag Levels

FVIIag levels can be measured with a commercial ELISA method, as described by Amiral, et al., *Clinical Chemistry* 30:1512 (1984) and available from Diagnostica Stago (Asnieres, France).

Applications of the Assay

The assay is designed for the measurement of plasma levels of factor VIIa in individuals, with primary application as a clinical diagnostic agent, particularly as a screening test in order to identify those individuals with elevated levels of factor VIIa. Such individuals are thought to have increased risk of thrombotic disorders. Furthermore, there may be other associations between elevated factor VIIa levels and disease that could be established with the use of this assay.

Another application for this assay is to monitor plasma factor VIIa levels in hemophiliacs and other individuals undergoing factor VIIa therapy. Recombinant factor VIIa therapy is currently in clinical trials.

1. Monitor Plasma Factor VIIa Levels in Patients Treated with Recombinant Factor VIIa Clinical trials of recombinant factor VIIa therapy for bleeding disorders are currently underway, but without a reliable and specific assay for measuring the resulting factor VIIa levels. The tTF assay provides a means for setting dose and monitoring efficacy in these patients.

2. Monitor Plasma Factor VIIa Levels in Patients Taking Oral Anticoagulants, Particularly Low-Dose Coumadin Therapy Patients on low-dose coumadin therapy show little change in clotting times in standard clotting assays, making it difficult to determine efficacy of the dose. For patients who respond to oral anticoagulant therapy with depressed factor VIIa levels, the tTF assay provides a means of monitoring such patients for efficacy, adjusting dose, etc.

3. Identify Individuals in the General Population with Increased Risk of Ischemic Heart Disease, Stroke, or Other Thrombotic Disease Recent studies have indicated a possible correlation between elevated factor VIIa levels and risk of such disorders as ischemic heart disease, as reported by de Sousa, et al., "Factor VII hyperactivity in acute myocardial thrombosis. a relation to the coagulation activation," *Thrombosis Research*, 51:165–173 (1988); Hoffman, et al., "Factor VII activity state in coronary artery disease," *J Lab Clin Med* 111:475–481 (1988); Gordon, et al., *J Lab Clin Med* 109: 409–413 (1987); and Mitropoulos, "Hypercoagulability and Factor VII in hypertriglyceridemia," *Seminars in Thrombosis and Hemostasis*, 14:246–252 (1988).

4. Screen Women During Pregnancy to Identify Those with Increased Risk of Complications of Pregnancy Factor VII coagulant activity normally rises during pregnancy. The assay may therefore be of use in screening the blood of pregnant women, since there are suggestions of a correlation between excessively elevated plasma factor VIIa levels and fetal growth retardation, as described by Scarabin, et al., "Is Factor VII activation in pregnant women relevant to fetal growth retardation?," *Thrombosis Research*, 45:845–850 (1987).

5. Screen Women Taking Oral Contraceptives to identify Risk Group for Thrombotic Complications Since FVIIc normally rises in pregnancy, it may also rise during use of oral contraceptives. It is possible that elevation of plasma factor VIIa could be an underlying cause of the thrombotic episodes that occur in some women using oral contraceptives. Alternatively, elevated factor VIIa levels in these women may be a marker of a "prethrombotic state". In either case, it is of clinical value to identify reliably a subpopulation of women who experience an excessive rise in factor VIIa levels when taking oral contraceptives.

6. Identify Individuals with Undetected Malignancy

Fibrin deposition and other indicators of activation of the coagulation system are frequently associated with malignant tumors. Elevated plasma factor VIIa levels may constitute a sensitive means of indicating the presence of otherwise undetected tumors.

7. Identify and/or Monitor Patients with Inflammatory Diseases, Sepsis, and Incipient DIC Activation of coagulation often accompanies inflammation, sepsis, and forms the basis of disseminated intravascular coagulation (DIC). Diagnosis of elevated plasma factor VIIa could serve as an early marker for these conditions.

8. Assess degree of thrombotic risk in patients who have diseases that are known or suspected to be associated with increased tendency toward thrombosis Plasma factor VIIa levels serve as an extremely sensitive indicator for activation of the clotting cascade in individuals; therefore, measuring factor VIIa can be used to help assess the actual thrombotic risk in patients who have diseases known to be associated with increased tendency toward thrombosis. Measuring factor VIIa levels may also be of value for monitoring effectiveness of anticoagulant therapy (or prophylaxis) in such individuals. Diseases with a known or suspected risk of thrombotic episodes include preeclampsia, hypertension, certain malignancies, hyperlipidemia, hypercholesterolemia, protein C deficiency, and unexplained recurrent venous and arterial thrombosis. In addition, monitoring factor VIIa levels may be of use during thrombolytic therapy of patients with acute myocardial infarction or stroke, and during and following vascular surgery, including angioplasty.

Modifications and variations of the compositions for assaying factor VII, and methods of use thereof, will be obvious to those skilled in the art from the foregoing detailed description. Such modifications and variations are intended to come within the scope of the appended claims.

---

I claim:

1. A kit for use in measuring factor VIIa in an anticoagulated plasma sample, comprising:
   (a) a truncated tissue factor reagent comprising truncated tissue factor and a phospholipid agent solubilized in an aqueous medium, said truncated tissue factor characterized by inability to bind to a phospholipid membrane surface and inability to support conversion of factor VII to factor VIIa while maintaining some cofactor activity, provided in a first container;
   (b) a factor VII-deficient plasma provided in a second container;
   (c) a factor VIIa standard provided in a third container; and
   (d) an instruction protocol for mixing said reagent with a plasma sample in an assay to measure an unknown amount of factor VIIa which may be present in said plasma sample, for mixing said reagent with said factor VIIa standard in said assay to measure a known amount of factor VIIa present in said standard, and for using said factor VII-deficient plasma as a diluent in said assay so that different concentrations of said plasma sample and of said standard can be measured.

2. The kit of claim 1, wherein said truncated tissue factor is from about amino acid 1–2 to between 209–222 of SEQ ID NO:2.

3. The kit of claim 1, wherein said truncated tissue factor is from about amino acid 1 to about 218 of SEQ ID NO:2.

4. The kit of claim 1, wherein said truncated tissue factor is from about amino acid 1 to about 219 of SEQ ID NO:6.

5. The kit of claim 1, wherein said truncated tissue factor is from about amino acid 1 to about 220 of SEQ ID NO:2.

6. A kit for use in measuring factor VIIa in an anticoagulated plasma sample, comprising:
   (a) a truncated tissue factor reagent comprising truncated tissue factor and a phospholipid agent solubilized in an aqueous medium, said truncated tissue factor characterized by its inability to bind to phospholipids and its inability to support conversion of factor VII to factor VIIa while maintaining some cofactor activity, provided in a first container;
   (b) a plurality of vials, each of said vials containing a known concentration of factor VIIa in a diluent comprising factor VII-deficient plasma, said plurality of vials providing a range of known factor VIIa concentrations from about 1 picogram per milliliter to about 10 microgram per milliliter; and
   (c) an instruction protocol for mixing said reagent with a plasma sample in an assay to measure an unknown amount of factor VIIa which may be present in said plasma sample, for adding said reagent to each of said vials in said assay and to measure a known amount of factor VIIa present in each of said vials.

7. The kit of claim 6, wherein said truncated tissue factor is from about amino acid 1–2 to between 209–222 of SEQ ID NO:2.

8. The kit of claim 6, wherein said truncated tissue factor is from about amino acid 1 to 218 of SEQ ID NO:2.

9. The kit of claim 6, wherein said truncated tissue factor is from about amino acid 1 to about 219 of SEQ ID NO:6.

10. The kit of claim 6, wherein said truncated tissue factor is from about amino acid 1 to about 220 of SEQ ID NO:2.

11. A kit for measuring the concentration of factor VIIa in an anticoagulated blood sample, comprising a soluble truancated tissue factor reagent dissolved in an aqueous diluent, said soluble truncated tissue factor characterized in that it does not bind to phospholipids and it does not promote the conversion of factor VII to factor VIIa while maintaining some cofactor activity, a phospholipid agent, and an instruction protocol for using said reagent in an assay for measuring factor VIIa in a plasma sample.

12. The kit of claim 11, wherein said reagent further comprises calcium ions.

13. The kit of claim 11, further comprising a separate vial containing a solution of calcium ions.

14. The kit of claims 11, wherein said aqueous diluent comprises factor VII-deficient plasma.

15. The kit of claim 11, wherein said truncated tissue factor is from about amino acid 1–2 to between 209–222 of SEQ ID NO:2.

16. The kit of claim 11, wherein said truncated tissue factor is from about amino acid 1 to about 218 of SEQ ID NO:2.

17. The kit of claim 11, wherein said truncated tissue factor is from about amino acid 1 to about 219 of SEQ ID NO:6.

18. The kit of claim 11, wherein said truncated tissue factor is from about amino acid 1 to about 220 of SEQ ID NO:2.

19. A kit for use in measuring factor VIIa in an anticoagulated plasma sample, comprising:
   (a) a truncated tissue factor reagent comprising truncated tissue factor solubilized in an aqueous medium, said truncated tissue factor characterized by inability to bind to a phospholipid membrane surface and inability to support conversion of factor VII to factor VIIa while maintaining some cofactor activity, provided in a first container;
   (b) a factor VII-deficient plasma provided in a second container;
   (c) a factor VIIa standard provided in a third container;
   (d) a phospholipid agent provided in a fourth container; and
   (e) an instruction protocol for mixing said reagent with a plasma sample in an assay to measure an unknown amount of factor VIIa which may be present in said plasma sample, for mixing said reagent with said factor VIIa standard in said assay to measure a known amount of factor VIIa present in said standard, and for using said factor VII-deficient plasma as a diluent in said assay so that different concentrations of said plasma sample and of said standard can be measured.

20. The kit of claim 19, wherein said truncated tissue factor is from about amino acid 1–2 to between 209–222 of SEQ ID NO:2.

21. The kit of claim 19, wherein said truncated tissue factor is from about amino acid 1 to about 218 of SEQ ID NO:2.

22. The kit of claim 19, wherein said truncated tissue factor is from about amino acid 1 to about 219 of SEQ ID NO:6.

23. The kit of claim 19, wherein said truncated tissue factor is from about amino acid 1 to about 220 of SEQ ID NO:2.

24. A kit for use in measuring factor VIIa in an anticoagulated plasma sample, comprising:
   (a) a truncated tissue factor reagent comprising truncated tissue factor solubilized in an aqueous medium, said truncated tissue factor characterized by its inability to bind to phospholipids and its inability to support conversion of factor VII to factor VIIa while maintaining some cofactor activity, provided in a first container;
   (b) a plurality of vials, each of said vials containing a known concentration of factor VIIa in a diluent comprising factor VII-deficient plasma, said plurality of vials providing a range of known factor VIIa concentrations from about 1 picogram per milliliter to about 10 microgram per milliliter;
   (c) a phospholipid agent provided in a second container; and
   (d) an instruction protocol for mixing said reagent with a plasma sample in an assay to measure an unknown amount of factor VIIa which may be present in said plasma sample, for adding said reagent to each of said vials in said assay and to measure a known amount of factor VIIa present in each of said vials.

25. The kit of claim 24, wherein said truncated tissue factor is from about amino acid 1–2 to between 209–222 of SEQ ID NO:2.

26. The kit of claim 24, wherein said truncated tissue factor is from about amino acid 1 to 218 of SEQ ID NO:2.

27. The kit of claim 24, wherein said truncated tissue factor is from about amino acid 1 to about 219 of SEQ ID NO:6.

28. The kit of claim 24, wherein said truncated tissue factor is from about amino acid 1 to about 220 of SEQ ID NO:2.

* * * * *

UNITED STATES PATENT AND TRADEMARK OFFICE
CERTIFICATE OF CORRECTION

PATENT NO. : 5,741,658
DATED : April 21, 1998
INVENTOR(S) : James H. Morrissey

It is certified that error appears in the above-indentified patent and that said Letters Patent is hereby corrected as shown below:

Column 1, line 7, after "5,472,850.", delete --+gi--.

Column 2, line 51, after "reality," change "FVIIC" to --FVIIc--.

Column 2, line 58, after "elevated" change "FVIIC" to --FVIIc--.

Column 3, line 30, after "it," delete --:--.

Column 7, line 16, after "TBS-EDTA" insert -- = --.

Column 10, line 56, after "between" change "100 $\mu$M" to --100 nM--.

Signed and Sealed this

Twentieth Day of October, 1998

Attest:

BRUCE LEHMAN

*Attesting Officer*     *Commissioner of Patents and Trademarks*